US00PP26044P3

(12) United States Plant Patent
Van Rosmalen

(10) Patent No.: US PP26,044 P3
(45) Date of Patent: Nov. 3, 2015

(54) *PHALAENOPSIS* ORCHID PLANT NAMED 'PHALCIQEQ'

(50) Latin Name: ***Phalaenopsis* Blume**
Varietal Denomination: PHALCIQEQ

(71) Applicant: ANTHURA B.V., Bleiswijk (NL)

(72) Inventor: Nicolaas Arnoldus Maria Van Rosmalen, Velp (NL)

(73) Assignee: ANTHURA B.V., Bleiswijk (NL)

( * ) Notice: Subject to any disclaimer, the term of this patent is extended or adjusted under 35 U.S.C. 154(b) by 154 days.

(21) Appl. No.: 13/998,196

(22) Filed: Oct. 10, 2013

(65) Prior Publication Data

US 2015/0106988 P1 Apr. 16, 2015

(51) Int. Cl.
*A01H 5/02* (2006.01)

(52) U.S. Cl.
USPC ..... Plt./311
CPC ..... *A01H 5/02* (2013.01)

(58) Field of Classification Search
USPC ..... Plt./311
See application file for complete search history.

(56) References Cited

PUBLICATIONS

Enclosure for the Plant Patent application of Anthura BV, 13 pages.

*Primary Examiner* — Anne Grunberg
(74) *Attorney, Agent, or Firm* — Jondle & Associates, P.C.

(57) ABSTRACT

A new and distinct variety of *Phalaenopsis* plant named 'PHALCIQEQ', particularly characterized by pink flowers with lighter shade and center and light pink lip with brown-orange shade and red stripes, 1 to 2 peduncles, a long and sturdy inflorescence, a narrow oblong leaf shape, and propagated by tissue culture is disclosed.

3 Drawing Sheets

Genus and species: *Phalaenopsis* Blume.
Variety denomination: 'PHALCIQEQ'.

BACKGROUND OF THE NEW PLANT

The present invention comprises a new and distinct cultivar of *Phalaenopsis* plant, botanically known as *Phalaenopsis* of the Orchidaceae family, and hereinafter referred to by the cultivar name 'PHALCIQEQ'.

*Phalaenopsis* comprises a genus of about 60 species of herbaceous perennials many of which, or the hybrids thereof, are suitable for cultivar in the home or greenhouse. *Phalaenopsis* is predominantly epiphytic or rock dwelling, and is native to tropical Asia, the Malay Archipelago, and Oceania. The species typically has 2-ranked, fleshy, oblong or elliptic leaves affixed to a short central stem (monopodial growth), which vary in size from 12 to 20 cm to over 60 cm. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petals, called the labellum, is three-lobed and is often more brightly-colored than the other flower segments. Flower colors include various shades of pink, white, yellow, and red-brown.

*Phalaenopsis* orchids are typically propagated from seeds. Asexual propagation of *Phalaenopsis* is often done from off-shoots which arise from the lower bracts of the inflorescence. The resulting plants are detached from the mother plants and may be planted in a suitable substrate.

The new *Phalaenopsis* 'PHALCIQEQ' is particularly characterized by its attractive and unique pink flowers, economical propagation by tissue culture, rapid growth, and a plant dimension suitable for packaging and shipping to the market and suitable only for 15 cm pot size.

'PHALCIQEQ' is a product of a planned breeding program conducted in Bleiswijk, The Netherlands.

The new *Phalaenopsis* 'PHALCIQEQ' originated from a cross made in October 2001 in Bleiswijk, The Netherlands. The female parent is a pink *Phalaenopsis* pot plant named '01-1276' (unpatented), while the male parent is a pink *Phalaenopsis* pot plant named '13848-01' (unpatented). A single plant was selected in November 2005 and has been asexually reproduced repeatedly by tissue culture in Bleiswijk, The Netherlands over a 7-year period. The new variety has been found to retain its distinctive characteristics through successive asexual propagations.

Asexual reproduction of 'PHALCIQEQ' by tissue culture was first performed in October 2009 in Bleiswijk, The Netherlands and has demonstrated that the new cultivar is firmly fixed and retained through successive generations of asexual reproduction.

Plant Breeder's Rights for this variety have been applied for in Europe on Jan. 15, 2013. 'PHALCIQEQ' has not been made publicly available or sold anywhere in the world more than one year prior to the filing date of this application.

SUMMARY OF THE INVENTION

The following are the most outstanding and distinguishing characteristics of this new cultivar when grown under normal horticultural practices in Bleiswijk, The Netherlands.

1) Pink flower with lighter shade and center and light pink lip with brown-orange shade and red stripes;
2) 1 to 2 peduncles;
3) Inflorescence is long and sturdy;
4) The shape of the leaf is narrow oblong; and
5) Plants are propagated by tissue culture.

DESCRIPTION OF THE PHOTOGRAPHS

This new *Phalaenopsis* plant is illustrated by the accompanying photographs which show the overall plant habit including blooms and foliage of the plant; the colors shown are as true as can be reasonably obtained by conventional photographic procedures. The photographs are of a 75-week old plant grown in a greenhouse in Bleiswijk, The Netherlands in May 2013.

DESCRIPTION OF THE NEW VARIETY

Figure 1:
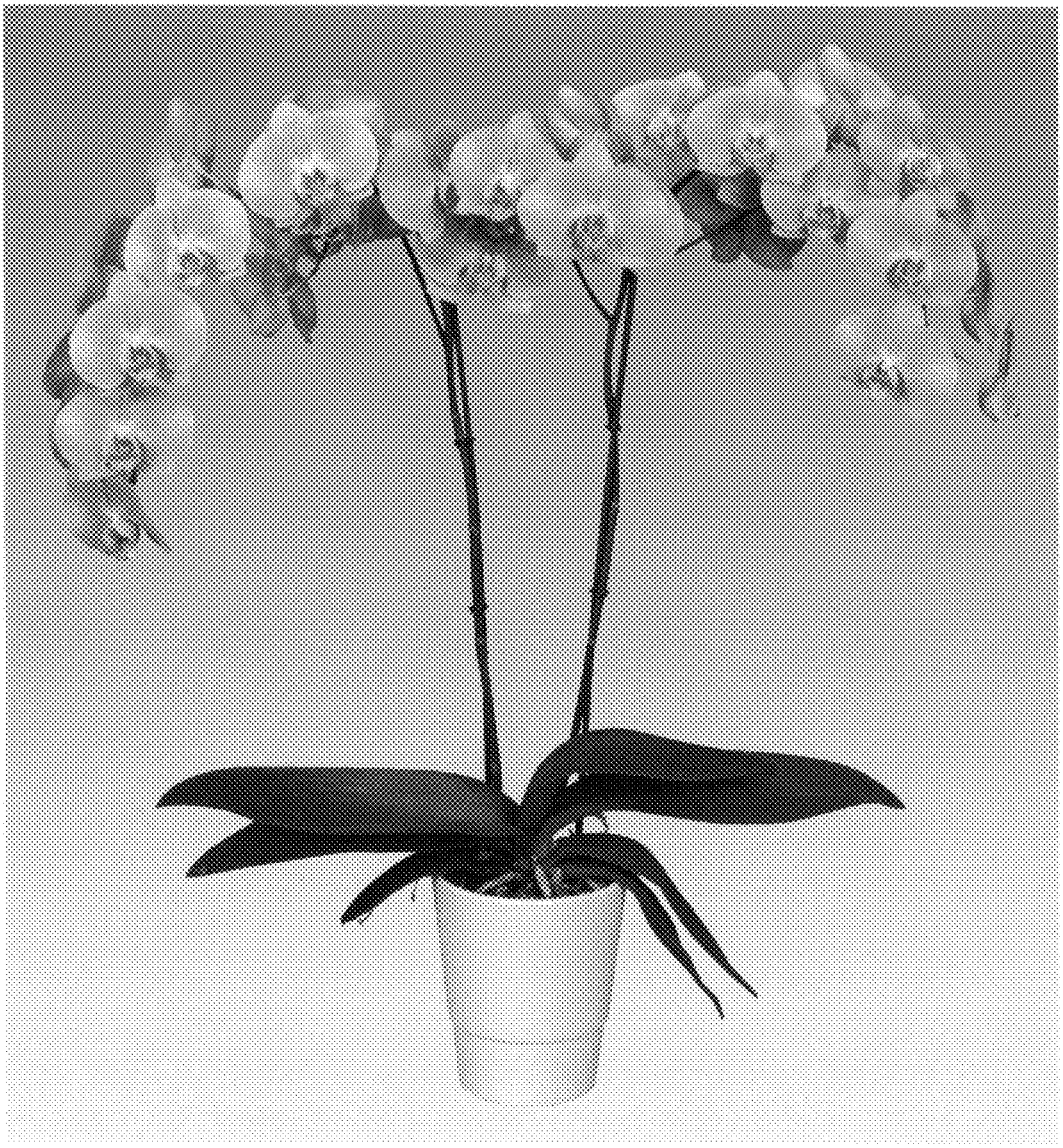
FIG. 1 shows the overall plant habit, including blooms and foliage of 'PHALCIQEQ'.
Figure 2:
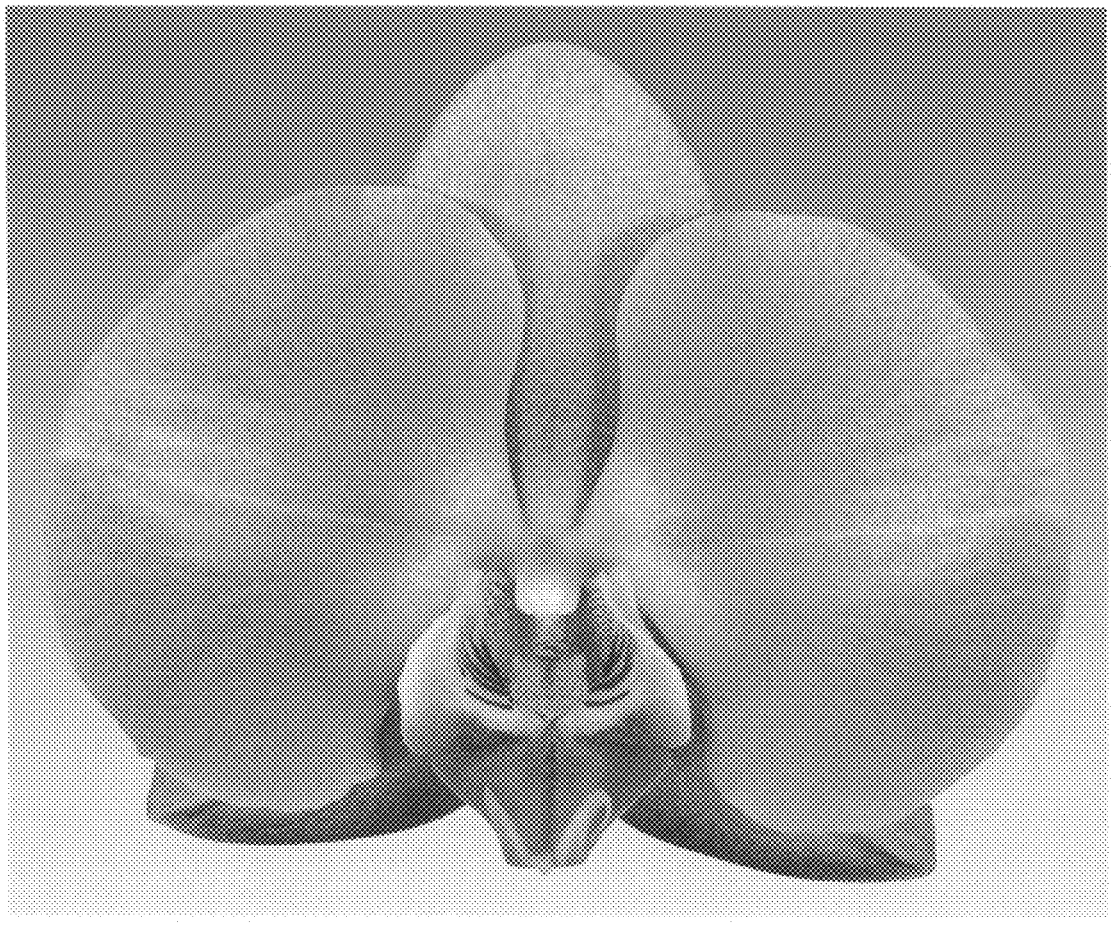
FIG. 2 shows a close-up of the flower of 'PHALCIQEQ'.
Figure 3:
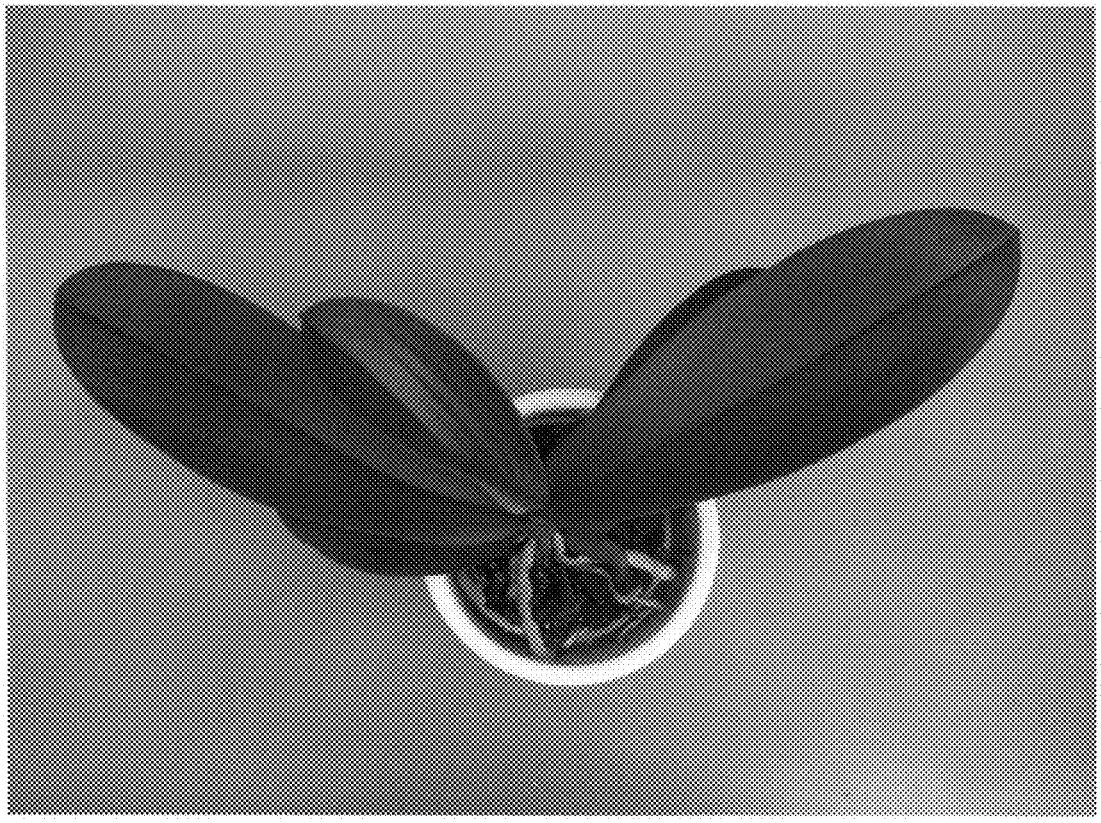
FIG. 3 shows a close-up of the leaves of 'PHALCIQEQ'.

The following detailed description sets forth the distinctive characteristics of 'PHALCIQEQ'. The data which define these characteristics were collected from asexual reproductions carried out in Bleiswijk, The Netherlands. The plant history was taken on 75-week old plants which were planted from tissue culture in 9 centimeter and 15 centimeter pots and grown in a greenhouse between 27° C. to 29° C. for 55 weeks, continued by a cooling period of 8 weeks between 18° C. to 20° C. and 12 weeks in a greenhouse of 21° C. Observations were made in May 2013. Color readings were taken under 5000 lux natural light in the greenhouse. Color references are primarily to The R.H.S. Colour Chart of The Royal Horticultural Society of London (R.H.S.) (2001).

DETAILED BOTANICAL DESCRIPTION

Classification:

*Family*.—Orchidaceae.

*Botanical*.—*Phalaenopsis* Blume.

*Common name*.—*Phalaenopsis*.

*Variety name*.—'PHALCIQEQ'.

Parentage:

*Female parent*.—*Phalaenopsis* cultivar '01-1276' (unpatented).

*Male parent*.—*Phalaenopsis* cultivar '13848-01' (unpatented).

Propagation:

*Type*.—Tissue culture.

Plant:

*Crop time* (*time to produce a finished flowering plant*).—65 to 70 weeks for a 15 cm pot.

*Growth habit of inflorescence*.—Standard type, green leaves and panicle.

*Height* (*including pot, including inflorescence*).—75.0 cm to 85.0 cm.

*Width* (*measured from leaf tips*).—50.0 cm to 56.0 cm.

*Vigor*.—Strong.

Roots:

*Root description*.—Grey-green-colored roots with branching lateral roots having grey-green-colored root tips.

Leaves:

*Mature leaves*.—Quantity per plant: 7 to 9 leaves are produced before flowering. Length (fully expanded): 26.0 cm to 30.0 cm. Width: 8.5 cm to 10.0 cm. Shape: Narrow oblong. Apex: Obtuse. Leaf blade angle with the petiole: Between 10 degrees and 25 degrees. Leaf margin: Entire. Color: Upper surface: RHS 147A. Lower surface: RHS 139C. Texture: Slightly rough. Thickness: 2.0 mm. Venation: Pattern: Parallel. Color of the midvein: Upper surface: RHS 139A. Lower surface: RHS 138A.

Peduncle:

*Quantity per plant*.—1 to 2.

*Number of flowers per peduncle*.—10 to 18.

*Length*.—65.0 cm to 75.0 cm.

*Diameter*.—About 0.8 cm.

*Strength*.—Strong.

*Aspect*.—Upright.

*Texture*.—Smooth.

*Color*.—Brown (RHS 200A).

*Internode length*.—60.0 mm to 130.0 mm.

Inflorescence description:

*Appearance*.—Upright to slightly pendant, panicle inflorescence with bilaterally symmetrical flowers that open in succession beginning with the lowermost flower.

*Inflorescence size*.—Height (from base to tip): 90.0 mm to 110.0 mm. Diameter: 220.0 mm to 250.0 mm.

*Flowering time*.—First flowers can be expected 16 to 17 months after planting in a 15 cm pot.

*Flower*.—Height: 75.0 mm to 80.0 mm. Diameter: 95.0 mm to 100.0 mm. Depth of lip: 24.0 mm to 26.0 mm.

*Flower longevity*.—On the plant: 19 to 21 weeks.

*Fragrance*.—Absent.

*Petals*.—Arrangement: Open. Shape: Semi-circular. Apex: Mucronate and symmetric. Margin: Slightly undulate. Length: 55.0 mm to 57.0 mm. Width: 44.0 mm to 46.0 mm. Color (when fully opened): Main color: Pink with lighter shade (RHS 78B; 78D). At the base: Pink with lighter shade (RHS 78B; 78D).

*Dorsal sepal*.—Shape: Elliptic. Length: 44.0 mm to 46.0 mm. Width: 29.0 mm to 31.0 mm. Color (when fully opened): Main color: Pink with lighter shade (RHS 78B; 78D). At the base: Pink with lighter shade (RHS 78B; 78D).

*Lateral sepals*.—Shape: Ovate. Length: 30.0 mm to 32.0 mm. Width: 44.0 mm to 46.0 mm. Color (when fully opened): Main color: Pink (RHS 78B). At the base: Pink with a yellow-green over color towards the center of the flower and red spots/dots (RHS 78B; 4D; 53A).

*Labellum* (*lip*).—Margin: Undulate. Length: 22.0 mm to 24.0 mm. Width: 23.0 mm to 25.0 mm.

*Lateral lobe*.—Shape: type V. Color: White with light pink and brown-orange shade and purple stripes (RHS 155C; 78D; 172D; 59A).

*Apical lobe*.—Shape: Obdeltoid. Color: Light pink with brown-orange shade (RHS 78D; 172D).

*Callus*.—Color: Yellow with red spots (RHS 21A; 60A).

Reproductive organs:

*Arrangement*.—The stamens, style and stigmas are fused into a single, short structure called the column, possessing one terminal anther with pollen grains united into pollinia, which are covered by an anther cap. The stigma is located under the column behind the pollinia. The ovary is inferior with three carpels present.

*Column*.—Length: 10.0 mm to 11.0 mm. Diameter: 5.0 mm to 6.0 mm. Color: White with pink shade (RHS 155C; 78D).

*Pollinia*.—Quantity: 2. Size: 1.0 mm to 1.1 mm. Color: Orange (RHS 24A).

*Ovary*.—Length: 9.0 mm to 10.0 mm. Diameter: 4.0 mm to 5.0 mm.

*Pedicel*.—Length: 40.0 mm to 60.0 mm. Diameter: 3.0 mm to 4.0 mm.

Disease, pest, and stress resistance: No specific resistance or susceptibility observed.

Temperature tolerance: Tolerant to a low temperature of 15° C. and a high temperature about 30° C.

COMPARISON WITH PARENTAL AND COMMERCIAL VARIETIES

'PHALCIQEQ' differs from female parent '01-1276' (unpatented) in that 'PHALCIQEQ' has a flower that is uneven, petals that are open/free, and a medium curvature of the lateral lobe, whereas '01-1276' has a flower that is even, petals that are almost touching to touching, and a strong curvature of the lateral lobe.

'PHALCIQEQ' differs from male parent '13848-01' (unpatented) in that 'PHALCIQEQ' has medium-sized whiskers, a white and slightly light lilac column, and a darker colored flower with a lighter shade, whereas '13848-01' has longer whiskers, a light purple column, and lighter colored flowers. Additionally, the apical lobe of the lip and the whiskers of 'PHALCIQEQ' are lighter colored than '13848-01'.

'PHALCIQEQ' differs from commercial variety 'PHALMACHE' (unpatented) in that 'PHALCIQEQ' has a flower with a small center that is shaded, a lighter pink apical lobe of the lip, and light purple whiskers, whereas 'PHALMACHE' has a flower with a larger center, a darker purple apical lobe of the lip, and dark purple whiskers. Additionally, 'PHALCIQEQ' has darker colored flowers than 'PHALMACHE'.

I claim:

1. A new and distinct variety of *Phalaenopsis* plant named 'PHALCIQEQ' as illustrated and described herein.

* * * * *